US010817722B1

(12) United States Patent
Raguin

(10) Patent No.: US 10,817,722 B1
(45) Date of Patent: Oct. 27, 2020

(54) SYSTEM FOR PRESENTATION ATTACK DETECTION IN AN IRIS OR FACE SCANNER

(71) Applicant: CROSS MATCH TECHNOLOGIES, INC., Palm Beach Gardens, FL (US)

(72) Inventor: Daniel H. Raguin, North Palm Beach, FL (US)

(73) Assignee: Cross Match Technologies, Inc., Palm Beach Gardens, FL (US)

(*) Notice: Subject to any disclaimer, the term of this patent is extended or adjusted under 35 U.S.C. 154(b) by 232 days.

(21) Appl. No.: 15/926,974

(22) Filed: Mar. 20, 2018

Related U.S. Application Data

(60) Provisional application No. 62/473,948, filed on Mar. 20, 2017.

(51) Int. Cl.
| | |
|---|---|
| *G06K 9/00* | (2006.01) |
| *G06F 21/32* | (2013.01) |
| *A61B 3/00* | (2006.01) |
| *A61B 3/10* | (2006.01) |

(52) U.S. Cl.
CPC ........ *G06K 9/00617* (2013.01); *A61B 3/0025* (2013.01); *A61B 3/102* (2013.01); *G06F 21/32* (2013.01); *G06K 9/00906* (2013.01)

(58) Field of Classification Search
CPC ... A61B 5/02416; A61B 5/681; A61B 5/4812; A61B 5/1123; A61B 5/02427
USPC ......... 382/117, 124; 713/176; 600/509, 549; 324/663, 549; 726/27
See application file for complete search history.

(56) References Cited

U.S. PATENT DOCUMENTS

| | | | |
|---|---|---|---|
| 4,924,506 A | 5/1990 | Crossley et al. | |
| 5,164,992 A | 11/1992 | Turk et al. | |
| 5,291,560 A | 3/1994 | Daugman | |
| 5,321,501 A | 6/1994 | Swanson et al. | |

(Continued)

FOREIGN PATENT DOCUMENTS

| | | |
|---|---|---|
| WO | WO2001/001329 | 1/2001 |
| WO | WO2016/055253 | 4/2016 |

OTHER PUBLICATIONS

Lee et al., Estimation of axial curvature of anterior sclera: correlation between axial length and anterior curvature as affected by angle kappa, BMC Ophthalmology, 16:176, pp. 1-11, 2016.

(Continued)

*Primary Examiner* — Charlotte M Baker
(74) *Attorney, Agent, or Firm* — Schwegman Lundberg & Woessner, P.A.

(57) ABSTRACT

A system for biometric security having a iris or face scanner for capturing biometric data over a first field of view of a subject, a topology scanner, and one or more processors utilizing the biometric data received from the biometric scanner to select one or more locations within the first field of view indicative of a biometric presentation to the biometric scanner, directing the topology scanner to capture topology data over a second field of view of the subject at one or more of the selected one or more locations, and determining in accordance with the topology data captured structures or measurements thereof, associated with ocular or extraocular features, to differentiate the subject between being fake and real in order to detect when the first field of view contains a possible fake presentation to the biometric scanner.

20 Claims, 11 Drawing Sheets

(56) References Cited

U.S. PATENT DOCUMENTS

| | | | |
|---|---|---|---|
| 5,493,109 | A | 2/1996 | Wei et al. |
| 5,751,836 | A | 5/1998 | Wildes et al. |
| 5,785,651 | A | 7/1998 | Kuhn et al. |
| 5,933,502 | A | 8/1999 | Aucsmith et al. |
| 5,991,429 | A | 11/1999 | Coffin et al. |
| 6,028,672 | A | 2/2000 | Geng |
| 6,057,920 | A | 5/2000 | Fercher et al. |
| 6,247,813 | B1 | 6/2001 | Kim et al. |
| 6,301,370 | B1 | 10/2001 | Steffens et al. |
| 6,542,624 | B1 | 4/2003 | Oda |
| 6,697,164 | B1 | 2/2004 | Babayoff et al. |
| 6,714,665 | B1 | 3/2004 | Hanna et al. |
| 6,940,891 | B2 | 9/2005 | Clary et al. |
| 6,983,062 | B2 | 1/2006 | Smith |
| 7,277,562 | B2 | 10/2007 | Zyzdryn |
| 7,440,590 | B1 | 10/2008 | Hassebrook et al. |
| 7,747,044 | B2 | 6/2010 | Baker et al. |
| 7,936,462 | B2 | 5/2011 | Jiang et al. |
| 8,391,590 | B2 | 3/2013 | Yalla et al. |
| 8,437,513 | B1 | 5/2013 | Derakhshani et al. |
| 8,494,829 | B2 | 7/2013 | Teixeira |
| 8,632,188 | B1 | 1/2014 | Gemoules |
| 8,687,856 | B2 | 4/2014 | Bower et al. |
| 9,163,936 | B1 | 10/2015 | Ulmer et al. |
| 9,280,695 | B2 | 3/2016 | Zyzdryn et al. |
| 9,396,382 | B2 | 7/2016 | Troy et al. |
| 9,784,561 | B2 | 10/2017 | Jiang et al. |
| 10,018,464 | B2 | 7/2018 | Boles et al. |
| 2006/0062438 | A1* | 3/2006 | Rowe ................. G06K 9/00046 382/124 |
| 2014/0283113 | A1* | 9/2014 | Hanna .................... G06F 21/32 726/27 |

OTHER PUBLICATIONS

Texas Instruments Inc., DLP® LightCrafter(TM) Evaluation Module (EVM), User's Guide, Nov. 2014.

Thorlabs Inc., Callisto 930 nm OCT Imaging System, printout from https://web.archive.org/web/20160909054413/https://www.thorlabs.com/newgrouppage9.cfm?objectgroup_id=3779, Sep. 9, 2016.

Cross Match Technologies, Inc., I Scan® 2, Compact Dual Iris Scanner, 2016.

Biometric Supply, Iritech IriShield—USB BK 2121U, Dual Iris Camera, printout from https://www.facebook.com/BiometricSupply/posts/678890372269709, Jun. 27, 2016.

Cheng, Y. et al., Artificial fingerprint recognition by using optical coherence tomography with autocorrelation analysis, Applied Optics, vol. 45, No. 36, pp. 9238-9245, Dec. 20, 2006.

Cambridge Technology, Ideal Scanning Solutions for Processing Large Areas, printout from https://web.archive.org/web/20161102190526/http://www.cambridgetechnology.com:80/products/3-axis-scan-heads, Nov. 2, 2016.

Cambridge Technology, 62xxH Series Galvanometer Scanners, 2016.

FLIR Integrated Imaging Solutions, Inc. (formerly Point Grey Research), Bumblebee® Stereo Vision Camera Systems, AutonomouStuff brochure, 2016.

Ximea GmbH, USB3 Vision Camera Series, Nov. 2014.

Ximea GmbH, USB 3.1 Gen 1 with Sony CMOS—xiC, printout from https://web.archive.org/web/20170305055513/https://www.ximea.com/en/products/usb-31-gen-1-with-sony-cmos-xic, Mar. 5, 2017.

Optotune AG, Dual axis mirror with position feedback MR-15-30, printout from https://www.optotune.com/products/beam-steering/2d-mirror-mr-15-30, 2016.

* cited by examiner

SYSTEM FOR PRESENTATION ATTACK DETECTION IN AN IRIS OR FACE SCANNER

This Application claims the benefit of U.S. Provisional Patent Application No. 62/473,948, filed Mar. 20, 2017, which is herein incorporated by reference.

FIELD OF THE INVENTION

The present invention relates to a system for presentation attack detection in an iris or face scanner, and particularly to a system for presentation attack detection using topology of the eye and/or face to determine whether the object(s) presented to such biometric scanner are real or fake. The topology is utilized by the system to determine structures or measurements thereof associated with ocular features, such as eye shape, sclera, iris, or caruncle, as well as of extraocular features, such as eyelid (location or thickness), nasal area, eyebrows, or eyelashes, for use in presentation attack detection.

BACKGROUND ON THE INVENTION

As the use of biometrics becomes increasingly ubiquitous in today's market, there is an increased threat of individuals attempting to circumvent implemented biometric security measures. With items being secured by biometrics (e.g., access to a government building, a border crossing, computer system, computer terminal, a bank account, etc.) becoming increasingly valuable, it is desirable to detect presentation attacks (PAs) on a biometric detection system. Often PAs are referred to as a "spoof", however PA as used herein is currently the more generally accepted term and refers to a presentation to biometric detecting systems that is fabricated to mimic that of a living human biometric. In other words, a true or real presentation or biometric presentation means the biometric presentation is coming from a human, while a false or fake presentation or biometric presentation means that the presentation is considered fabricated to mimic that of a human biometric, but is not a human biometric and preferentially not a live human biometric. Often the physical mechanism by which a PA is implemented (e.g., a membrane of silicone with an imprint of a fingerprint or a glass eye ball) has been termed a "spoof", however the more current terminology is an "artifact" or a presentation attack instrument (PAI).

Presentation attack detection (PAD) methods for iris biometrics in the current art include a variety of approaches. For example, U.S. Pat. No. 5,933,502 (Aucsmith et al.) describes the use of having randomly selected light sources that illuminate an object such as a face or an eye and monitor the reflected light coming back to ensure that a PA such as a printed photo of a face or iris is not in play. U.S. Pat. No. 6,542,624 (Oda) describes an iris PAD technology based upon initiating a response of the eye based upon stimuli. Oda describes providing dark and bright environments in order to trigger the pupil to increase or decrease in diameter as well as providing a visual target that moves and monitoring movement in the eye that for a real eye would occur regardless of whether or not the real eye is intentionally or not tracking the target. Oda also proposes the blowing of air at the eye to initiate and measure an eyelid response. U.S. Pat. No. 8,437,513 (Derakshani et al.) also describes the use of tracking eye movement between successive frames of an iris scanner camera based upon the presentation of a moving visual target as well as to look for photo-initiated reactions of the eye to help determine if an iris presentation is true or false.

International PCT Publication No. WO 01/01329 A1 by Seal et al. describes three methods of potentially distinguishing if iris presentations are true or false. In one method, light substantially parallel to the imaging axis illuminates the eye and the appearance of red-eye is observed. For example, there will be no red-eye effect if the iris presentation is a printed image, or even a glass eyeball with iris printed is presented, but behind the pupil. The second method described by Seal et al. is the observance of a corneal-cross or the Maltese cross which is an optical effect with polarized light that can be observed in a real eye because of the anisotropy of the eye's materials which is not present in a photo of an eye. The third method that Seal et al. describes is the use of projected light patterns. By illuminating the eye with a pattern of light (a distinctive pattern of one or more straight and parallel lines), Seal et al. describes that one can identify if a subject is presenting a real iris or presenting a fake iris where the fake iris is printed onto a contact lens. As illustrated in Seal et al. as presented in FIGS. 6A and 6B herein, Seal et al. describes that one may observe that for a real iris 101a of an eye 100a, the light pattern 102a is straight across the iris 101a, as in FIG. 6A, but that for a fake iris 101b of an eye 100b with such fake iris, printed onto a contact lens, one observes curvature, FIG. 6B, of the light pattern 102b. While Seal et al. describes the use of a single light pattern, it does not teach the actual measurement of topology. As such, Seal et al. does not utilize topology measurement for determination of an iris PA.

U.S. Pat. No. 9,396,382 (Troy et al.) describes the use of three-dimensional (3D) scanning system based upon structured light imaging (SLI), but does not utilize the 3D topology measured of the biometric presentation in order to identify whether or not that presentation is true or false. Rather Troy et al. describes the use of captured color image data to determine if the reflectivity as well as the color spectrum of the object being presented is consistent with that of normal human skin.

SUMMARY OF THE INVENTION

Accordingly, one object of the present invention is to provide a system for presentation attack detection in an iris or face scanner which utilizes topology of the eye and/or face to determine whether the object(s) presented in the field of view of such biometric scanner are real or fake.

It is another object of the present invention to provide a system for presentation attack detection in iris or face scanners in which the topology is provided by a three-dimensional imager.

Briefly described, the present invention embodies a system having a biometric scanner for capturing biometric data over a first field of view of one or both eyes or face of a subject, a topology scanner, and one or more processors utilizing the biometric data received from the biometric scanner to select one or more locations within the first field of view indicative of a biometric presentation to the biometric scanner, directing the topology scanner to capture topology data over a second field of view of the subject at one or more of the selected one or more locations, and determining in accordance with the topology data captured structures or measurements of ocular or extraocular features to differentiate the subject between being fake and real in order to detect when the first field of view contains a possible fake presentation to the biometric scanner.

The system may be provided in an apparatus having a housing with the biometric scanner, the topology scanner, and the one or more processors. The one or more processors control the operation of the biometric scanner and topology scanner in accordance with software or program. An optional computer may be provided in the system connected to the one or more processors, and may represent one of the processors in the system since the computer can optionally process, or assist in processing, the data from biometric scanner and the topology scanner.

The topology scanner is a three-dimensional (3D) imager or scanner, such as an optical coherence tomography imager, a laser scanner, or a structured light imager, to scan at one or more of the selected locations along the eye or face and provide to the one or more processors topology data in the form of image data. From such image data received, the one or more processors determines structures or measurements thereof related to ocular features, such as one or more of eye shape, sclera, iris, or caruncle, or extraocular features (i.e., features near the eye) of one or more of eyelids, nasal area, eyebrows, or eyelashes to differentiate the subject between being fake and real. The one or more processors compares each of one or more measurements determined with one or more of a threshold or ranges stored in memory of, or accessible to, the one or more processors, expected of a human associated with such structures to differentiate the subject between being fake and real.

The 3D imaging provided by the topology scanner may further be provided by a stereo imager that relies upon measured parallax between images taken by two cameras separated by a certain distance but looking at the same object. Alternatively, a confocal scanner may be utilized which images through pinholes in order to image successive planes at different distances from the scanner. A time-of-flight system may be implemented where the time it takes for light to strike certain points of an object and reflect back to a sensor are recorded and the time differences measured related to the topology of the object according to the speed of light. Optionally, the topology scanner may encompass multiple imagers or scanners of different modalities for acquiring topology data for use by the one or more processors for presentation attack detection.

The second field of view of the topology scanner and overlaps at least a portion of, the first field of view of the biometric scanner, and the first and second fields of view are spatially correlated with each other for enabling the one or more processors to direct the second field of view of the topology scanner to capture topology data at one or more of selected one or more locations along the subject. The second field of view may be the same or smaller than the first field of view.

The biometric data from the biometric scanner used to select such one or more locations may represent image data of the same or different, such as lower resolution, than needed in performing identity management for enrollment, identification or verification of a subject in a biometric security system that controls access to physical and/or electronic environments. If the biometric data is acceptable for identity management, then it may be used by the one or more processors in the apparatus or the external computer to identify the identity of the subject when the first field of view is determined by the system to contain a true presentation to the biometric scanner. Otherwise, biometric scanner captures over said first field of view new biometric data that is acceptable for identity management.

The present invention further embodies a method for biometric security comprising the steps of capturing biometric data with a biometric scanner over a first field of view of a subject having at least one eye of the subject, selecting one or more locations using the biometric data within the first field of view indicative of a biometric presentation to the biometric scanner, directing a topology scanner to capture topology data over a second field of a subject at one or more of the selected one or more locations, and determining in accordance with the topology data captured when the first field of view contains a possible fake presentation to the biometric scanner.

The present invention also embodies an apparatus having the above described system.

The present invention still further embodies a system which uses the topology of a subject's sclera for presentation attack detection or for identification, either as a sole biometric identifier or more preferentially in combination with one or more other biometrics, identification card, or password/PIN.

BRIEF DESCRIPTION OF THE DRAWINGS

The foregoing and other objects, features, and advantages of the invention will become more apparent from a reading of the following description in connection with the accompanying drawings in which.

DETAILED DESCRIPTION OF THE INVENTION

Figure 1:
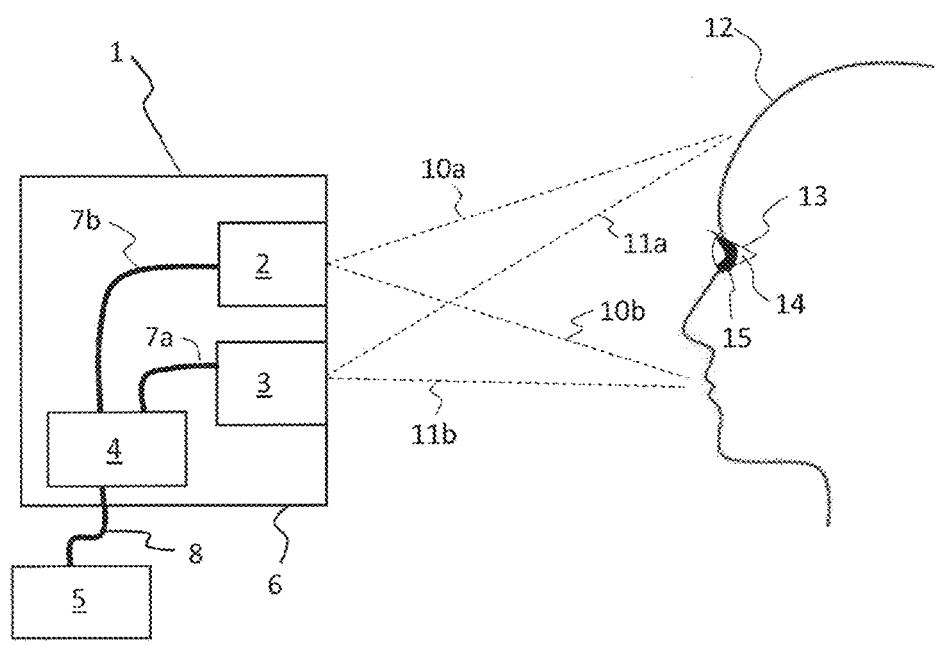
FIG. 1 depicts a schematic diagram of the system of the present invention having a biometric scanner and topology scanner shown with respect to a subject.

Referring to FIG. 1, a block diagram of a system 1 of the present invention is shown. System 1 may be provided in an apparatus having a housing 6 with a biometric scanner (system or module) 2 and a topology scanner (system or module) 3 which are connected to a processor 4 via cables 7a and 7b. The biometric scanner 2 and the topology scanner 3 may be separate modules as drawn or may be integrated within one another. Processor 4 represents one or more processors in housing 6 for controlling the biometric scanner 2 and topology scanner 3 and may process all or some of the data received from the modules. An optional computer 5 connected via cable 8 (or wirelessly) to processor 4 may represent one or more of processors 4 in system 1 since the computer can optionally process, or assist in processing, data from biometric scanner 2 and the topology scanner 3 in accordance with software operating computer 5. For example, one or more processors providing processor 4 in housing 6 may be of an electronic type and may contain one or more data processors (or chips), or a central processing unit (CPU), such as an ARM (Advanced RISC Machine) processor, a digital signal processor (DSP), or a field programmable gate array (FPGA) operating in accordance with software or program. However, other programmable logic devices may be used for processor 4, which may represent a module in housing 6. Memory may be provided in the processor 4, or in the housing 6 accessible by the processor for storing such software or program. Computer 5 shown external of housing 6 has a user-interface (e.g., a software program with a graphical user interface (GUI), keyboard and/or mouse). While the term program is used, such program may represent one or more programs stored in memory for use by one or more processors providing processor 4 in system 1. Power is supplied via battery within, or external power source to, housing 6 to enable electronics of system 1 as typical of an iris or face scanning system which may provide biometric scanner 2, but adapted to include topology scanner 3 in providing system 1.

The biometric scanner 2 may be one or more of an iris scanner and a face scanner having a field-of-view (FOV) denoted by dashed lines 10a and 10b. The biometric scanner 2 provides image or image data of a biometric presentation 12, such as a human face, or one eye or both eyes, captured with sufficient quality to perform iris or face enrollment, identification, and/or verification. The topology scanner 3 may be separate as illustrated or integrated with biometric scanner 2. Topology scanner 3 has a FOV denoted by dashed lines 11a and 11b where such FOV has substantial overlap with the FOV of biometric scanner 2. For the purposes of presentation attack detection (PAD), the topology scanner 3 is directed to image or scan one or more locations of biometric presentation 13, such as the eye 13, the sclera 14 and iris 15. The image captured by biometric scanner 2 for purpose of directing the topology scanner 3 may be of the same quality as used for biometric detection, but need not be of such sufficient quality. For example, biometric scanner 2 may have the primary goal of being an iris scanner that conforms to ISO/IEC 29794-6-2013 which specifies that sufficient quality requires ≥15.7 pixels/mm at the eye. However, for face recognition, Neurotechnology (Vilnius, Lithuania), a company that markets fingerprint, iris, and face recognition software, recommends at least 64 pixels across the interpupillary distance (IPD). Taking the minimum IPD of a subject to be 52 mm, this only amounts to ~1.2 pixels/mm to recognize a face. The biometric scanner 2 may therefore initially capture a low-resolution image for the purposes of directing topology scanner 3 to chosen location (s) of biometric presentation 12. However, if the biometric image data provided by the biometric scanner 2 can be used for both identification of such location(s) for PAD and also biometric identification acceptable for use for biometric security, then biometric identification may take place in parallel with PAD, if desired, rather than after PAD has validated the biometric presentation as being true.

Examples of iris or face scanner providing the biometric scanner 2 in system 1 are described in U.S. Pat. No. 5,751,836 (Wildes et al.), U.S. Pat. No. 6,247,813 (Kim et al.), U.S. Pat. No. 6,714,665 (Hanna et al.), U.S. Pat. No. 5,991,429 (Coffin et al), or U.S. Pat. No. 5,164,992 (Turk et al.), which are incorporated herein by reference. However, other iris or face scanners may be used, such as an ISCAN2 dual iris scanner from Crossmatch (Palm Beach Gardens, Fla.), a BK2121U dual iris scanner from Iritech, Inc. (Fairfax, Va.), as well as multi-megapixel cameras such as those included in a smartphone for face scanning.

The topology scanner 3 obtains topology data of an object or a portion of an object in its FOV. By way of example, topology scanner 3 may operate by one or more of structured light imaging (SLI), laser scanning, stereo vision, confocal microscopy, or OCT. The topology scanner 3 in the case of confocal scanner or OCT scanner has depth resolution of at least 1 mm into tissue and may be used to determine that a potential biometric presentation is not a picture or a video replay attack. Preferentially, such depth resolution is 100 µm or better so that the shape of the sclera and thickness of the eyelids can be determined. Still preferentially, the topology scanner 3 has resolution of at least 10 µm such that better metrology data can be collected of the iris to such that any departure of the iris from being real can be determined.

The topology scanner 3 may be a scanner or imager as described in the following patents which are incorporated herein by reference: a SLI scanner as described in U.S. Pat. No. 7,440,590; a laser scanner as described in U.S. Pat. No. 9,163,936 or 6,940,891; stereo vision scanner as described in U.S. Pat. Nos. 4,924,506, 6,028,672, or 6,301,370; an OCT scanner as described in U.S. Pat. Nos. 5,493,109, 6,057,920, 5,321,501, or 8,632,188; or a confocal scanner for ocular imaging as described in U.S. Pat. No. 5,785,651 (Kuhn et al) or U.S. Pat. No. 6,697,164 (Babayoff et al.). Commercial topology scanners or imagers may also be utilized for topology scanner 3, such as for example, the Callisto 930 nm spectral domain, an OCT imaging system available from ThorLabs, Inc. (Newton, N.J.), Bumblebee XB3 and Bumblebee2 stereo vision cameras available from FLIR Systems, Inc. (Wilsonville, Oreg.), and structured light imagers available from FlashScan3D LLC (San Antonio, Tex.). The biometric scanner 2 and/or topology scanner 3 may represent modules in housing 6 each with electronics which communicate with the one or more processors providing processor 4 in accordance with manufacturers of such scanners 2 and 3 to obtain biometric image data and topology data, respectively, in system 1.

Figure 2A:
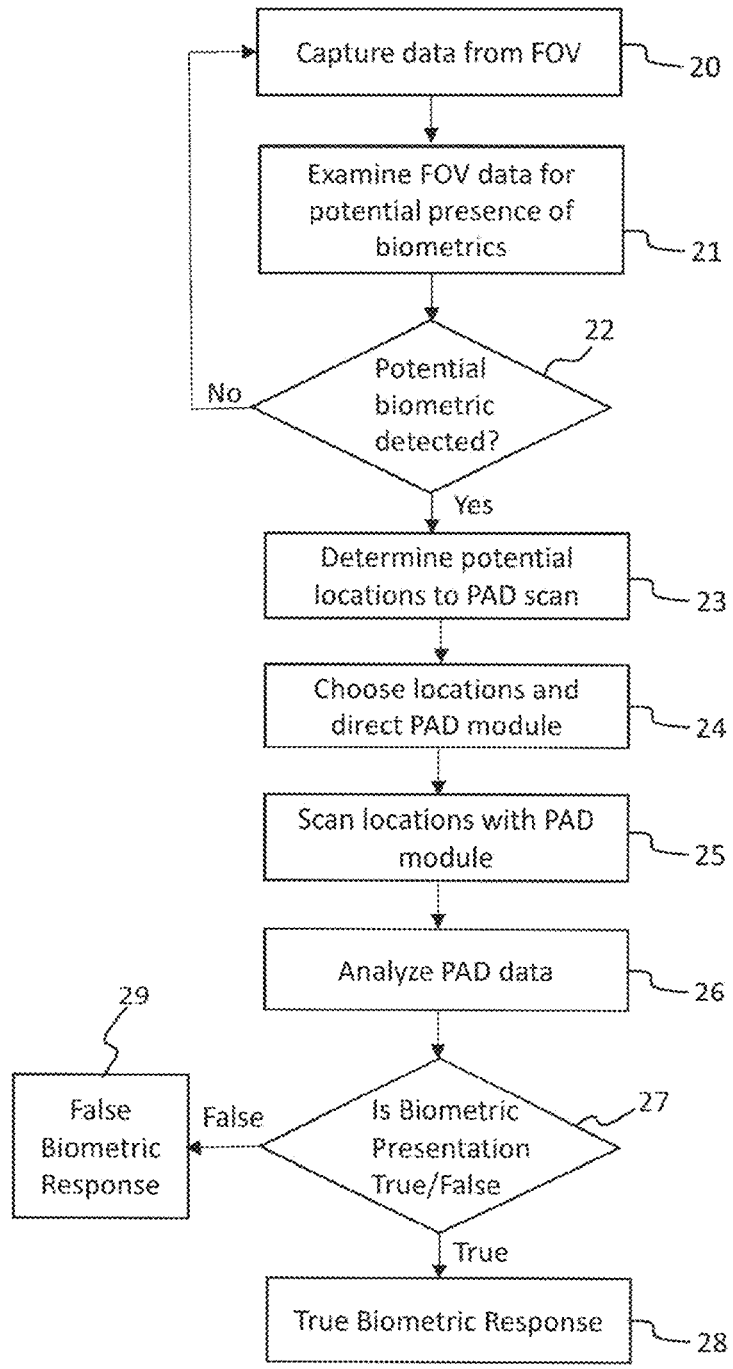
FIG. 2A is a flowchart illustrating the operation of the system of FIG. 1.

The operation of system 1 is shown in the flow chart of FIG. 2A. In step 20, the biometric scanner 2 captures biometric data within its FOV. This biometric data may be any form of data, such as optical, infrared, radio, radar, capacitance, resistance, ultrasound, impedance, temperature, or pressure. The biometric data captured is stored in memory of, or accessible to, processor 4 and/or optional computer 5. The biometric image data captured in step 20 need not be sufficient to capture a biometric presentation capable of biometric identification for performing enrollment, identification or verification, but just needs to be sufficient to determine whether or not a biometric presentation is likely to be in the FOV of the biometric scanner 2. For example, the initial biometric data collected at step 20 for determining if a biometric presentation is present may be made using a different modality than that of the final biometric data required for identity management. For example, the initial biometric data collected in step 20 might be collected using thermal imaging or ultrasound range detection, while the final biometric data collected for identify management may require an optical image. Similarly, the initial biometric data collected at step 20 might be captured with the image capture modality as needed for biometric image data for identity management, but may not have all the same criteria. For example, the initial biometric data collection at step 20 used for PAD and final biometric data collection used for identity management may be performed with a near infrared (NIR) camera providing biometric scanner 2, where the initial biometric collection mode at step 20 uses a low-level steady state NIR illumination with a long camera pixel integration in order to detect the presence of a face or iris, while for final biometric capture mode (after the biometric presentation is determined to be true) the system 1 switches biometric scanner 2 to a short pulse NIR illumination and short pixel camera integration time in order to suppress ambient light effects on the eye and achieve a better face or iris image for identity management. Thus, while biometric data captured by the biometric camera 2 at step 20 may be image data, biometric scanner 2 may operable in different modes, or represent more than one biometric scanner, one scanner enabling capture of a biometric image data for identity management and another a scanner/imager that provide biometric data at step 20 enabling steps 21-23 as described below.

In step 21, the stored biometric data from step 20 is analyzed via processor 4 and/or optional computer 5 to determine if a biometric presentation (i.e., biometric feature(s) or object(s) associated with the biometric scanner 2) might be present. By way of example, such processing can be through iris location as described in U.S. Pat. No. 5,751,836 (Wildes et al.). The system 1 at step 22 then makes a decision if a biometric presence is detected. If no biometric presence is detected, the system will go back to step 20 and the biometric scanner 2 will continue to collect biometric data within its FOV. If there is a biometric presence detected, the process flow moves to step 23 where the potential location(s) of a biometric presence are calculated and then in step 24 the actual location(s) to scan are determined (or selected) and the topology scanner 3 is directed towards those location(s) to obtain topology data for subsequent PAD analysis at step 26. The detecting of each of one or more biometrics (objects or structures in field of view in the biometric presentation) in the biometric data of scanner 2 and locations thereof of steps 22 and 23 is performed by processor 4 and/or computer 5 by image processing received biometric data from biometric scanner 2 in the form of a two-dimensional image of pixels of grayscale values to locate boundaries of objects. This may be performed by gradient detection and/or local thresholding (differentiation from the background by a desired grayscale threshold value) to locate boundaries of object(s) that follow the general form of biometric associated with biometric scanner 2. However, other imaging processing methods to locate desired objects in images may also be performed, such as the use of Hough transforms to find circular boundaries as well as those techniques described in U.S. Pat. No. 5,291,560 (Daugman), U.S. Pat. No. 5,751,836 (Wildes et al.), U.S. Pat. No. 9,280,695 (Zyzdryn et al.), U.S. Pat. No. 6,983,062 (Smith), or U.S. Pat. No. 7,277,562 (Zyzdryn).

In the directing of topology scanner 3 of step 24 to each selected location, either the entire physical topology scanner 3 moves or a portion of the topology scanner 3 moves in order to direct the topology scanner 3 scans. Optionally, topology scanner 3 only scans those one or more locations selected within its FOV without need to move scanner 3 with respect to particular locations in presentation 12. By way of example, topology scanner 3 may be mounted to a linear translation stage or a set of orthogonal translation stage in order to bring its FOV in-line with selected location(s). In another example, the topology scanner 3 may have an optical beam that probes the biometric presentation 12 and just this beam is swept across the FOV of the biometric scanner 2 and not the entire scanner 3, such as described below in connection with FIGS. 8 and 9. In still a further example, the FOV of the topology scanner 3 may substantially overlap with the FOV of the biometric scanner 2 so that no physical movement of any portion of the topology scanner 3 is required. Rather any location the topology scanner is directed to analyze for PA's are then localized as a region of interest. As a clarifying example of this, system 1 may have an iris scanner providing biometric scanner 2 and a structured light projector providing topology scanner 3 that encompasses the entire FOV of the iris scanner. The structured light projector is then windowed by processor 4 and/or optional computer 5 to provide topology data or image only to the region of interest that encompasses the location selected, or in the subsequent image analysis the topology data is cropped down to the desired location before being analyzed at step 26.

Figure 3:
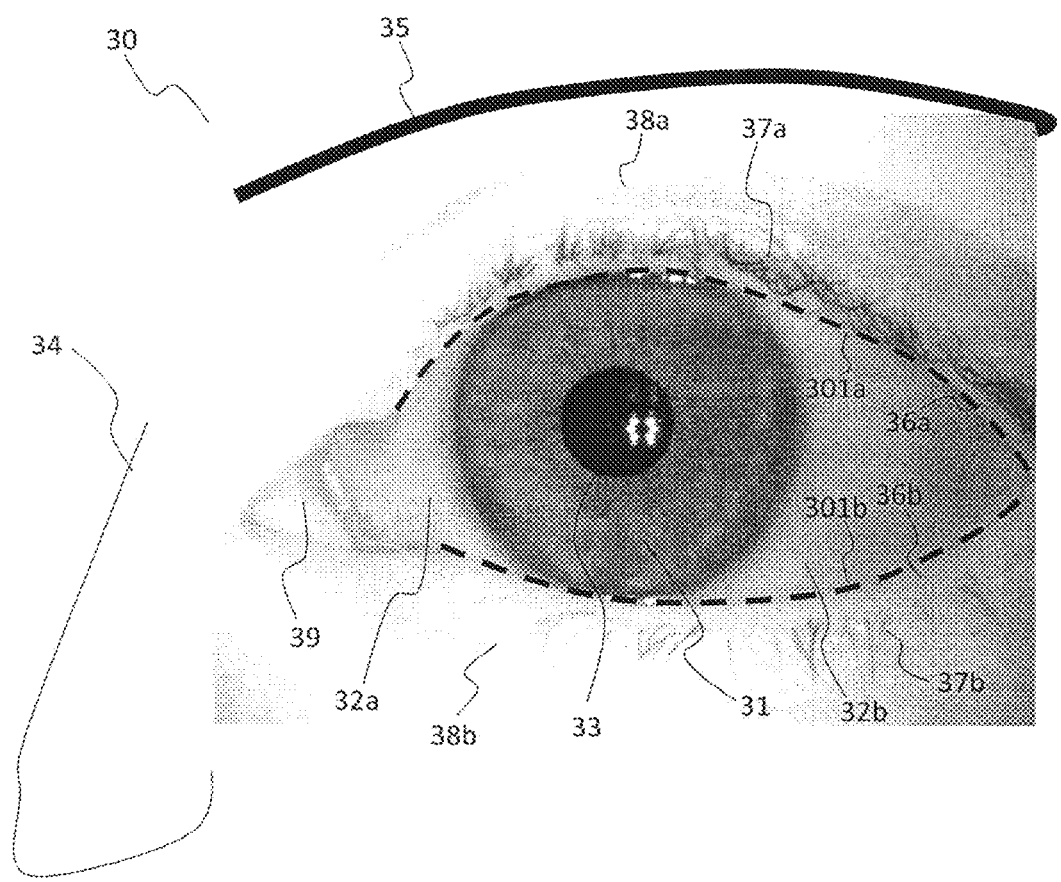
FIG. 3 depicts an example of captured image data by the biometric scanner in the system of FIG. 1 from which locations are identified for scanning by the topology scanner of the system.

To clarify the locations that the topology scanner 3 may scan, consider FIG. 3 which represents an optical image 30 captured at step 20 roughly centered about a human eye. For the purposes of PAD detection, one or more locations such as the iris 31, sclera (nasal side 32*a* and temporal side 32*b*), eyelids, eyelashes (upper 37*a* and lower 37*b*), the lacrimal caruncle 39 and the nose 34 can be selected locations at step 24 that can be used for PAD analysis at step 26. The eyelids (upper 38*a* and lower 38*b*), thickness of the eyelid (upper 36*a* and lower 36*b*), and eyebrows 35 may also be selected locations by processor 4 and/or computer 5 as well. Note that all of the locations denoted in FIG. 3 may not require scanning by the topology scanner 3. For example, the scanning at step 25 may be performed sequentially and if after scanning two locations and finding conclusive evidence that the two scanned locations are either true biometrics or false biometrics, the process flow might move to the next step. Alternatively, if the first two scanned locations give weak evidence one way or another that the biometric presentation is true or false, maybe a third or even fourth location is designated as being required for scan.

Figure 2B:
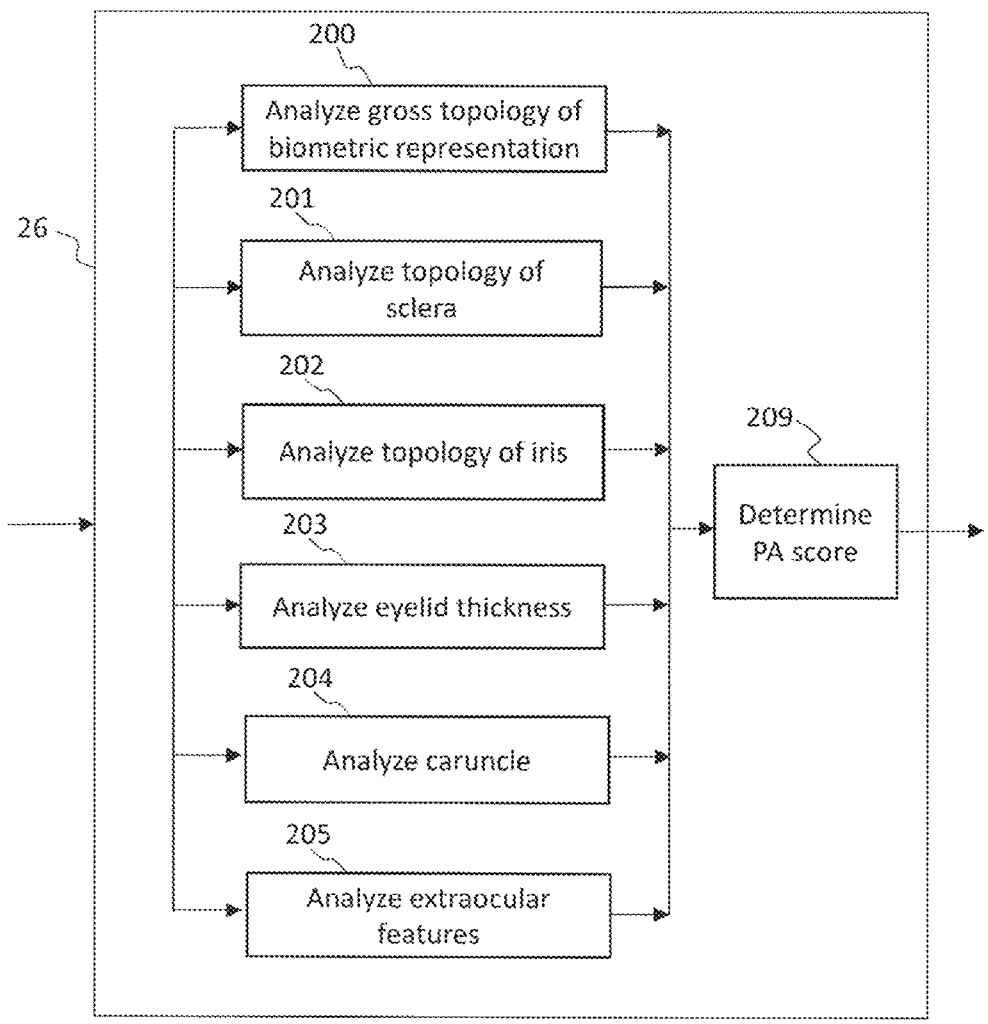
FIG. 2B is a flowchart of the presentation attack analysis using one or more ocular and/or extraocular features of step 26 of FIG. 2A.

The PAD data analysis (step 26) conducted by processor 4 and/or optional computer 5 involves outputting a PA score that measures the possibility that the locations of the possible biometric presentation represent a true biometric or a false biometric. To illustrate the logic of the PAD data analysis step 26, a flow chart is depicted in FIG. 2B. The analysis performed may involve digital analysis in processor 4 and/or optional computer 5 to analyze the topology of gross features (step 200), sclera (step 201), iris (step 202), eyelid thickness (step 203), caruncle (204), and extraocular features (step 205). Each of these aforementioned steps may be conducted more than once, for example the sclera of a biometrics left and right eye may be analyzed. A subset of these aforementioned steps may be used or other steps be added to topologically analyze different features of the biometric presentation to arrive at a PA score.

In step 200, the analysis of gross topology of the biometric presentation, by way of example, may involve analyzing the topology of the presentation, fitting it to a best fit plane and looking at the departure of the data from this plane. If there is less than one mm departure, than the analysis concludes the presentation is too flat to be a real presentation and must be a PA and probably a stiff photo or video display. The analysis may perform spatial frequency correlation to the plane-fit topology data. Rather than looking for a minimum departure of the fit topology data from a plane (which could be met if the photo of the iris or face is purposely bent into a curve), certain topological slopes may be required. Such slopes would be indicative of the curvature of the sclera, the high-frequency topology of eyelids or eyebrows, as well as the sharp jump in topology at the eyelid. Alternatively, analysis of the gross features of the biometric presentation may include capturing the 3D topology of the presentation and running it through a low-pass filter such as convolving it with a 2D Gaussian kernel. The convolved image can then be subtracted from the original image and the average root mean squared departure in topology across the image calculated. If this average root mean squared number is low, then the original presentation had extremely course features such as would be present in a printed photo of an iris or the use of a video attack with a cell phone, resulting in a very high PA score (assuming the higher the PA score the more likely the presentation is an attack).

Figure 4:
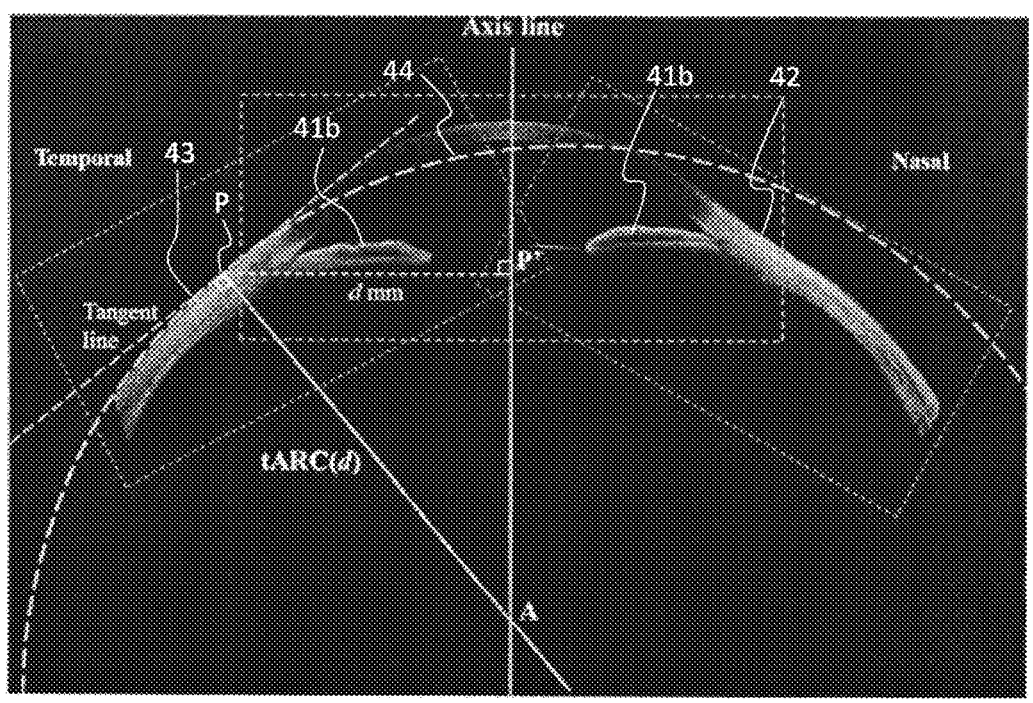
FIG. 4 depicts an example of captured image data by the topology scanner of the system of FIG. 1, where such topology scanner is provided by an OCT image scanner, showing a cross-section OCT scan of a human iris in order to illustrate the non-spherical curvature of the sclera and the non-flat topology of an iris for use in presentation attack detection.
Figure 5:
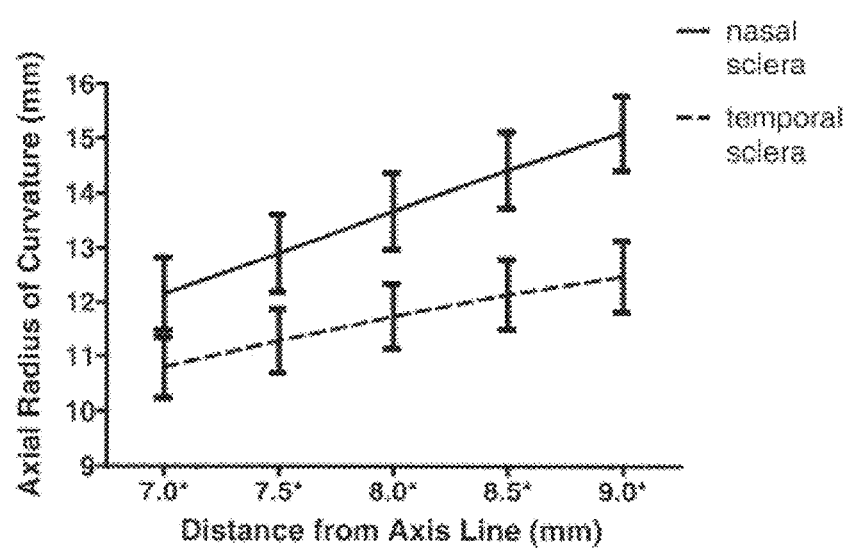
FIG. 5 is a chart illustrating the local radius of curvature at different points across the sclera for the right eyes of 24 human subjects to show the non-spherical nature of the sclera topology of the eye as well as the difference in curvature between the nasal and temporal sides of the sclera.

In step 201, the analysis of the sclera can first analyze the sclera region of the biometric presentation to determine if it fits a plane or cylinder and therefore is more likely a photo or video replay or does it come closer to fitting a sphere or a toroid and then is more indicative of a real human sclera. Note that in performing the curve fit of the sclera it may be preferred to fit the nasal side of the sclera 32a to one sphere or toroid and the temporal side of the sclera 32b to another sphere or toroid since the two sides of the sclera are different as is evident from the data graphed in FIG. 5. Preferentially if the accuracy of the topology scanner 3 is sufficient, in step 201 the fitting of the sclera profile to an aspheric freeform is conducted. As illustrated in FIG. 4, the temporal sclera 43 at a point P may be fit to a sphere 44, but this best-fit sphere at point P is not a good fit to the rest of the temporal sclera or the nasal sclera 42. As illustrated in FIG. 5, the local best fit sphere radius at various points P that are at different axial distances from the pupil (namely from 7 to 9 mm distances) are graphed based upon OCT data taken from both the nasal and temporal sides of the sclera. This data is collected and averaged from the right eyes of 24 Asian subjects (12 men, 12 woman) with an age range of 31.3±6.5 years. As FIG. 5 indicates, the average axial radius changes as a function of distance from the pupil indicating an aspheric profile (the lines would be flat at a constant axial radius if the cornea where spherical) and further that the cornea is more of a free-form it is not symmetric about the pupil center, but rather has different aspheric terms on the nasal side and the temporal side. FIGS. 4 and 5 are copied from Lee et al., "Estimation of axial curvature of anterior sclera: correlation between axial length and anterior scleral curvature as affected by angle kappa", BMC Ophthamology, 16:176 (2016).

Optionally, as an additional or sole biometric detection parameter, the unique topology, i.e., three-dimensional (3D) contour, obtained of a person's sclera may be used as a biometric identifier. This may involve digital processing by mapping the 3D contour of the sclera to a template, such as the coefficients necessary to construct an aspheric geometric toroid, for enrollment, identification, and verification, in the same manner as other biometric identifiers, as fingerprints, iris, or face in a typical biometric security system. Preferably, the sclera of a person would be part of a multi factor authentication, such as in combination with one or more other biometric identifiers, identification card, or password/PIN.

Figure 6A:
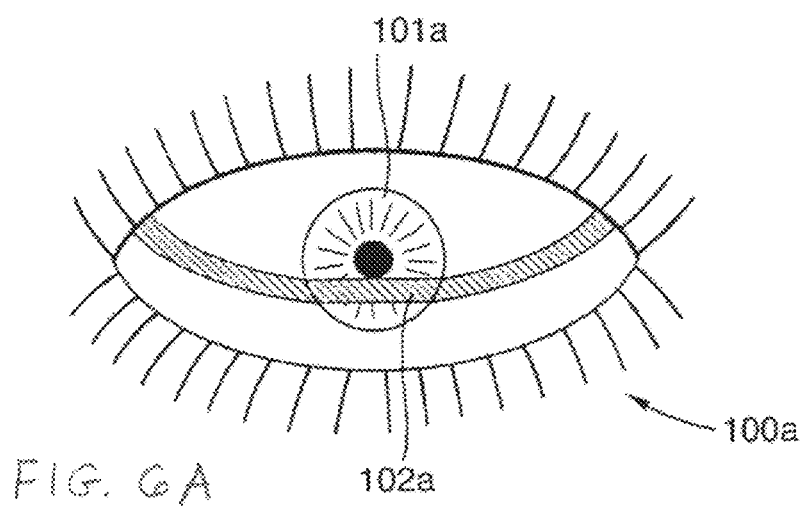
FIG. 6A is an illustration of the eye showing a straight line of illuminating light when viewed at an angle appears curved across a real human sclera, but straight across a human iris.
Figure 6B:
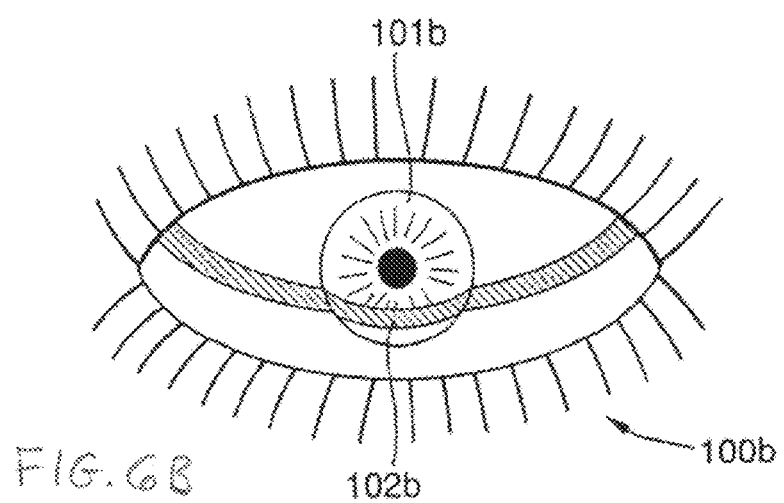
FIG. 6B is an illustration of the eye showing a straight line of illuminating light when viewed at an angle appears curved across a real human sclera, but also curved across the iris portion of the image when the subject is wearing a contact lens that has a printed iris pattern.

In step 202, the analysis of the iris can perform an initial test to determine if the iris is grossly flat or grossly curved as discussed in PCT Publication No. WO 01/01329 (Seal et al.), with regards to FIGS. 6A and 6B. The test may be such as described by Seal et al. where a curved projected line across the iris indicates a PA while a flat one indicates a real iris. As stated earlier, one may observe that for a real iris 101a of an eye 100a, the light pattern 102a is straight across the iris 101a, as in FIG. 6A, but that for a fake iris 101b of an eye 100b with such fake iris, printed onto a contact lens, one observes curvature, FIG. 6B, of the light pattern 102b. Alternatively the topology of the iris in the form of a 3D point cloud can be fit to a plane and the departure from a planar profile analyzed. The analysis by processor 4 and/or optional computer 5 may look at the peak-valley departure of the best plane fit data and if the departure is larger than a certain value, than the iris is not a real iris, but a fake one, and may for example be an iris that was printed onto a contact lens and which is not curved and resting on a human's cornea as a PA. In order to distinguish between a real iris and now a printed iris that is behind a glass or plastic cornea replica, the PAD performed in processor 4 and/or optional computer 5 determines whether the spatial frequency topological modulations that present are consistent with a real human iris.

Figure 7:
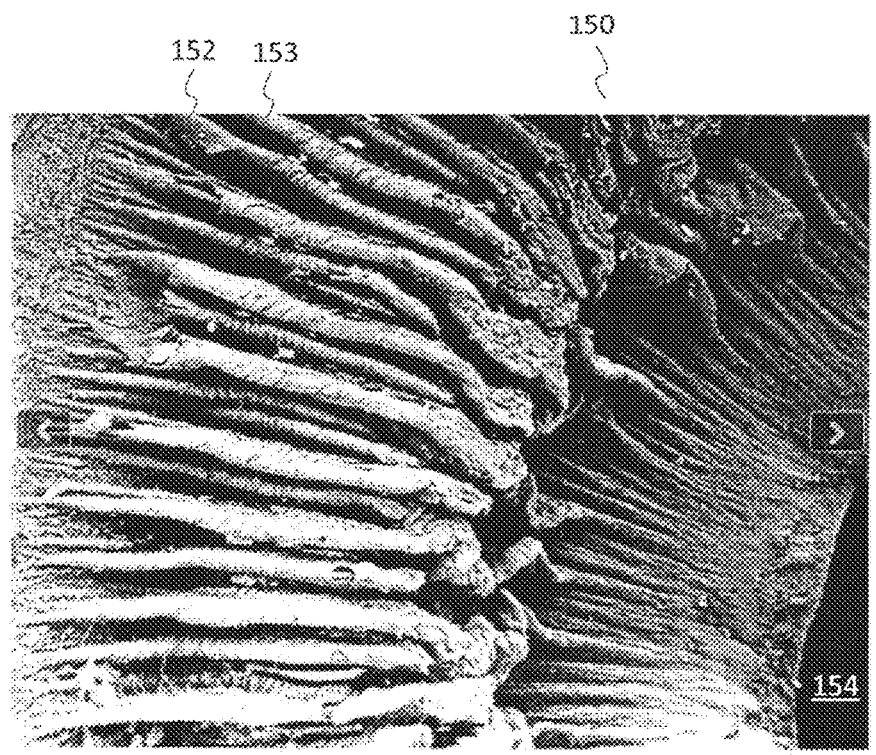
FIG. 7 is a scanning electron microscope image (SEM) of a human iris illustrating its 3D topology.

As illustrated in FIG. 4, the iris 41b is not flat and has some sub-mm topology. The fine features of the iris are easily observed in FIG. 7 where a scanning electron microscope (SEM) image 150 of a human iris is depicted. The human iris tends to have numerous folds (two of which 152 and 153 are marked) that run radially from the center of the pupil 154. The iris analysis at step 202 may therefore preferentially look at the polar power spectrum of the image in order to discern ranges of angular frequencies that are consistent with those expected in humans. Alternatively, or in addition to, a Cartesian power spectrum may analyzed at step 202 and look for anomalous power spectrum frequency components since a human iris does not have spatial frequencies that tend to run along Cartesian axes, while an iris fabricated with an x-y printer or plotter would in general.

An additional step that may be integrated into the overall PA score is one that analyzes the eyelid thickness, step 203. As illustrated in FIG. 3 by dashed line 36a and 36b, there is a rather sharp topology change where the upper and lower eyelids, respectively meet the sclera. This sharp change in topology may be analyzed and if not present, such as in a glass eyeball held by a stick or not present across a smooth curved line 301a and 301b, the biometric presentation may be classified as a PA. Curved lines 301a and 301b may be curve fit to a circle or to an asphere and compared to the range of curvatures at the eyelid to sclera/cornea boundary for typical humans as stored in memory of, or accessible to, processor 4, which if outside such range may indicate a PA. The profile of the eyelid boundary as well as the topological thickness along the curvature of the iris may be fused into a single PA score. Further, an additional step that may be integrated into the overall PA score is one that analyzes the presence of the caruncle, step 204. The caruncle is indicated at 39 in FIG. 3.

An additional step that may be integrated into the overall PA score is one that analyzes the presence of the extraocular features such as the nasal area 34, eyebrows 35, eyelids 38*a* and 38*b* and eyelashes 37*a* and 37*b*, at step 205. For this analysis, PAD by processor 4 and/or optional computer 5 may first finding the center of the pupil or iris as described in U.S. Pat. No. 5,291,560 (Daugman) and then looking in the expected area that the extraoccular features are expected in the biometric presentation to system 1. In the case of the eyebrows and eyelashes, the PAD by processor 4 and/or optional computer 5 may check for certain spatial frequency in the topological data indicative of these features. The analysis may also incorporate the original image of the biometric scanner captured at step 20 using NIR illumination and look at such image for certain features via edge detection or local or global thresholding. As illustrated in FIG. 3, eyebrows and eyelids are much darker than other features of the eye (other than the pupil) when illuminated in the NIR. The expected measurements (threshold(s) or ranges) thereof at steps 200-205 used to compare with measured biometric characteristics to distinguish fake or real biometrics may be stored in memory of, or accessible by, processor 4 and/or optional computer 5.

After performing one or more of steps 200 through 205, the results must be combined or fused into a single PA score that is output by process step 26. The determination of a single PA score is conducted in step 209. For further clarifications of exemplary fusion techniques, see U.S. Pat. No. 7,747,044 (Baker et al.), or U.S. Pat. No. 8,494,829 (Teixeira). By way of example, the PA score may have a range of 0 to 100 and the higher the score, the more likely the biometric presentation is a PA. The score thresholds that triggers a true or false PA decision (step 27) is subject to the use case for system 1, i.e., its particular biometric security application. For access control to a building that is not necessarily high security or where multi-factor authorization is used (for example, a fingerprint is not the only form of identification required, but maybe an RFID badge and PIN are also required), then it may be better to set the PA threshold higher and have a higher False Accept Rate (FAR) and lower False Reject Rate (FRR). Conversely for a high-security use case, the PA threshold may be set such that FAR is very low (i.e., less likely that a false biometric presentation will be accepted as true) with the tradeoff that FRR is higher (chance that a real biometric presentation is scored to be a false presentation). Again, dependent upon the use case, the response for a false biometric (step 29) and the response for a true biometric (step 28) may vary. For example, for step 29, a detection of a false biometric may sound an alarm, require the subject to pass several additional steps to prove an identity otherwise not required for a true biometric detection, or may just simply not allow the subject to pass a locked access point. For step 28 a true biometric decision at least some of the next steps involve taking the biometric data scanned or biometric scanner 2 capturing additional biometric data needed to confirm identity of the subject. For example if in step 20 only 1.2 pixel/mm optical data was taken to determine if a biometric presentation occurred, after determining that this presentation was true (step 27) the system may require now 16.7 pixel/mm NIR optical biometric data be captured in order to ascertain a biometric identity via iris template matching. As such the identity of the subject may be determined by the same image data as is captured at step 20, or recaptured at higher resolution image data if needed, when step 27 has determined that true biometric objects, rather than the fake ones, are in the presentation to the biometric scanner 2. The image data for identity management may be received by a biometric security system for matching with a database of biometric stored data for a population of subjects enrolled to access identity so as to control access to physical and/or electronic environments, in a manner typical of identification, verification, or enrollment in biometric based security systems available from Cross Match Technologies, Inc. of Palm Beach, Fla., USA. System 1 in addition to detecting a presentation attack may be part of, or represents, such biometric security system for identity management, where computer 5 provides software with a user interface for enabling same, and memory storing, or accesses via a network, the database.

Figure 8:
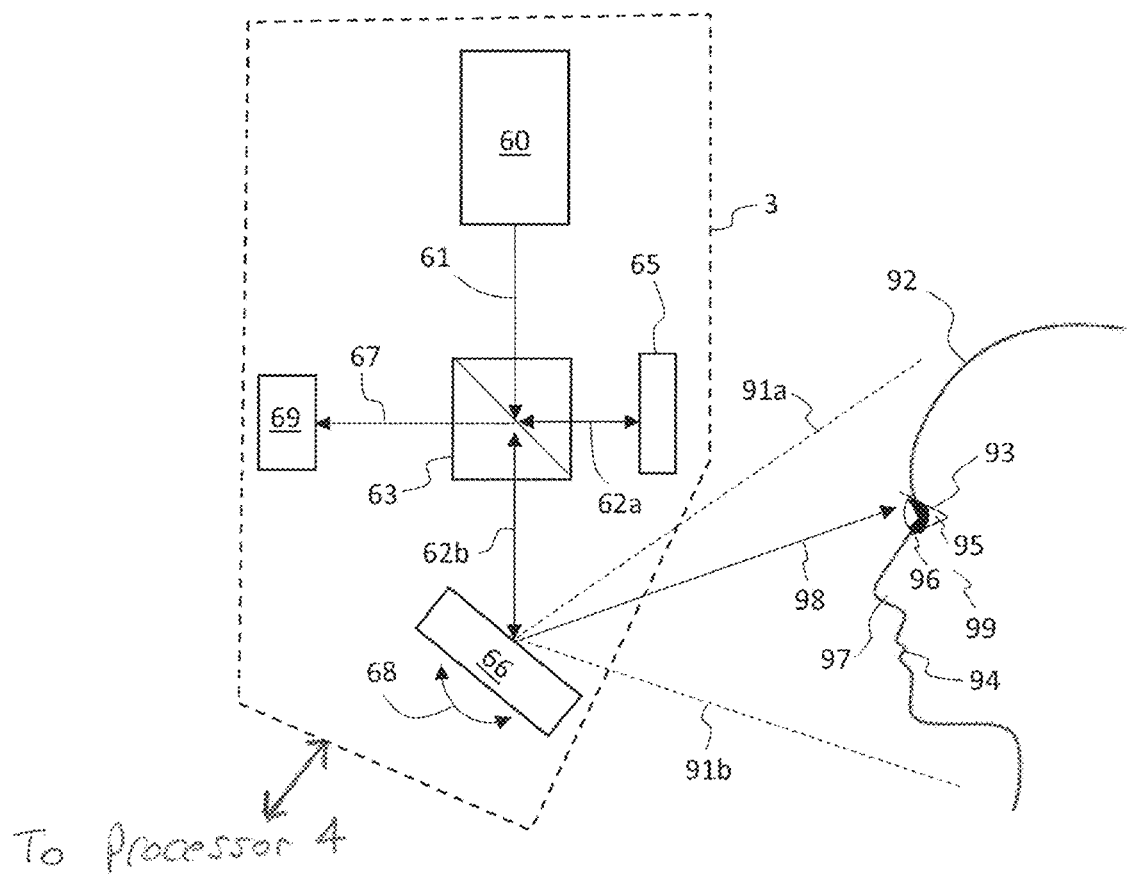
FIG. 8 is a block diagram of the topology scanner of the system of FIG. 1 utilizing an OCT image scanner, in which the OCT scanner has a movable mirror which directs imaging of the OCT scanner to one or more selected locations within the field of view of the biometric scanner.

Referring to FIG. 8, the topology scanner 3 of system 1 is illustrated utilizing an optical coherence tomography (OCT) scanner head to provide topology data for step 26 PAD analysis in order that step 27 determination can be made as to whether or not the biometric presentation is true or false. The OCT scanner head is composed of a superluminescent light-emitting diode (SLED) light source 60 with an optical output beam 61 that is split into two beams 62*a* and 62*b* via a beamsplitter 63. The reference path traveled by beam 62*a* reflects off of a mirror 65 while the object path traveled by object beam 62*b* strikes another mirror or mirrors 66 mounted on a mechanism that allows rotation of the mirror in the direction 68 such that the reflected beam 98 can sweep the FOV of the scanner 2 given by dashed line boundaries 91*a* and 91*b*. Note that FIG. 8 is drawn in two dimensions and so direction 68 appears to be just in a single plane, however in general, the movement of mirror(s) 66 may be more than one axis, thereby enabling not just a one dimensional sweep of beam 98 across biometric presentation 92, but a two-dimensional sweep. The mechanism for moving the mirrors 66 to steer beam 98 to step 25 selected location(s) for scanning may consist of tip or tip-tilt galvanometers (such as available from Cambridge Technology of Bedford, Mass., USA) or two-dimensional mirrors based upon electroactive polymers (such as available from Optotune of Dietikon, Switzerland). The use of galvo mirrors for directing the FOV of an optical system are described in U.S. Pat. No. 6,714,665 (Hanna et al.) and U.S. Pat. No. 5,751,836 (Wildes et al.). Alternatively, the topological scanner 3 may have a set of x-y mechanical stages to move the OCT measurement head to measure any location or substantially all of the locations in the FOV of the biometric scanner 2. Thus, beam 98 steering can be conducted using one-dimensional or two-dimensional mirrors 66 such as those mounted to a galvanometer or a pair of galvanometers, as desired for the particular application of system 1. Wires or cables connect processor 4 to power and enable diode 60, as well as to control the position control electronics for mirror(s) 66 and other electronics of the OCT scanning head. Since OCT modules operate on the principle of coherence, it is important that the optical path length (OPL) of the reference arm matches the location of the biometric presentation (including a certain depth into the presentation if it is desired to scan the interior structure of the presentation) that is being scanned. As such, reference mirror 65 is generally scanned to change the OPL of the reference path to match that of the object path where said scanning may be accomplished a variety of ways such as by mounting mirror 65 onto a high-precision (resolution on the order of 10 um or better) stage.

The light reflected back from the object(s) in each selected location in biometric presentation 92 being scanned (traveling the same path as beam 98 and 62b) reenters scanner 3 and is combined by beam splitter 63 with light from the reference path into a single beam 67 that is imaged onto a sensor 69. For more detailed regarding OCT scanners, refer to Cheng and Larin "Artificial fingerprint recognition by using optical coherence tomography with autocorrelation analysis," Appl. Opt. 45, pp. 9238-9245 (2006), U.S. Pat. No. 8,687,856 (Bradley et al.), U.S. Pat. No. 5,493,109 (Wei), U.S. Pat. No. 6,057,920 (Fercher et al.), or U.S. Pat. No. 5,321,501 (Swanson et al.). As stated earlier, OCT scanner systems which may be adapted for system 1 include the Callisto 930 nm spectral domain OCT imaging system sold by ThorLabs, Inc. (Newton, N.J.). OCT systems such as Callisto that operate in the near Infrared. Reflectance (NIR) are good for imaging beneath the surface of human tissue since human tissue is penetrated more easily by NIR wavelengths than visible wavelengths.

As previously discussed when referring to FIG. 3, depending upon the form of PAD analysis at step 26 and the FOV the topology scanner 3, different selected locations at step 24 within the presentation 92 of the human head or eye(s) may be checked for the possibility of a PA. By way of example, where biometric scanner 2 captures a single or dual iris biometric data at step 20, the topology scanner 3 may be directed to scan one or more of an iris 96, a portion of the sclera 95, or the entire eye 93. Scanner 3 may scan these locations sequentially as well, for example scanning the iris first and if the PA test is inclusive, scan the sclera, etc. For a face biometric scanner 2, the topology scanner 3 may be directing each beam 98 to analyze, by way of example, one or more of the nose 97, mouth 94, and cheekbones 99 of the presented face 92 in order to determine the topology of these features and if they are consistent with what is expected for a human biometric presentation as described earlier for PAD analysis at step 26.

Figure 9:
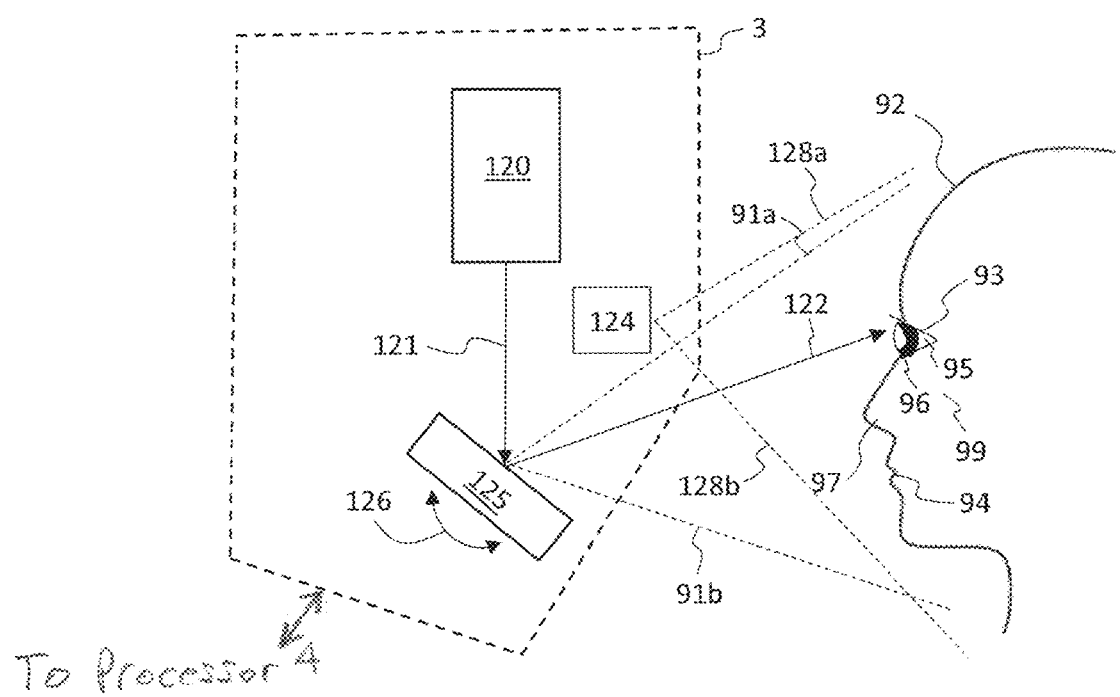
FIG. 9 is a block diagram of the topology scanner of the system of FIG. 1 utilizing a laser scanner.

Referring to FIG. 9, the topology scanner 3 of system 1 is illustrated utilizing an optical scanner head comprising a light source 120, such as a laser, a scanning mirror 125, and an optional camera 124. Light source 120 has an emitted optical beam 121 that reflects off of scanning mirror 125 where mirror 125 is capable of being moved bidirectionally as denoted by arrow 126. Mirror 125 may be same types of movable mirror(s) 66 as discussed earlier in reference to FIG. 8. Mirror 125 may be capable of being moved in one axis or two axes, thereby enabling either tip or tip/tilt motion and the mirror mechanics may be those of a galvanometer. Mirror 125 is thereby able to direct reflected beam 122 within field-of-view designated by dashed lines 91a and 91b towards the biometric presentation 92 at one or more of the locations identified at step 24 (FIG. 2) selected with the best chance of identifying a PA. The interaction point at which beam 122 hits biometric representation 92 is detected either by an optional optical digital camera 124 in system 1 (that has field-of-view designated by dashed lines 128a and 128b) or by the imaging system of biometric scanner 2 (FIG. 1) to captures image(s) providing topology data for use by processor 4 and/or optional computer 5 at step 26.

The imaging system of biometric scanner 2 or optional camera 124 in FIG. 9 may have an objective lens (for example an f=35 mm with a C-mount), such as those from Azure Photonics (Fuzhou, China) that captures an image of the biometric presentation 92 onto a detector such as a CMOS (complementary metal-oxide semiconductor) or a CCD (charge-couple device) detector, where such detector is integrated with the appropriate electronics to communicate digital image data as topology data for use by processor 4 and/or optional computer 5. An example of camera 124 is available from Ximea (Munster, Germany), and preferably camera 124 is the 5 MP Sony CMOS sensor based USB 3.0 Ximea Model MC050MG-SY when using a single camera to capture an image of both irises simultaneously, or the USB3.0 Ximea model MQ013MG-ON camera that uses an e2V 1.3 MP CMOS sensor if it is a single-iris in the field of view. Other laser scanning topology scanners may also be used for topology scanner, including 3D profilometers as described in the following herein incorporated by reference patents: U.S. Pat. No. 9,163,936 (Ulmer et al) and U.S. Pat. No. 6,940,891 (Clary et al.). U.S. Pat. No. 9,163,936 refers to applications of laser scanning profilometers that include the measurement of the human sclera for purposes of constructing a scleral lens or an ocular surface prosthetic. Wires or cables connect processor 4 to power and enable light source 120, as well as to control the position control electronics for mirror(s) 125 and other electronics of the laser scanner of FIG. 9.

Figure 10:
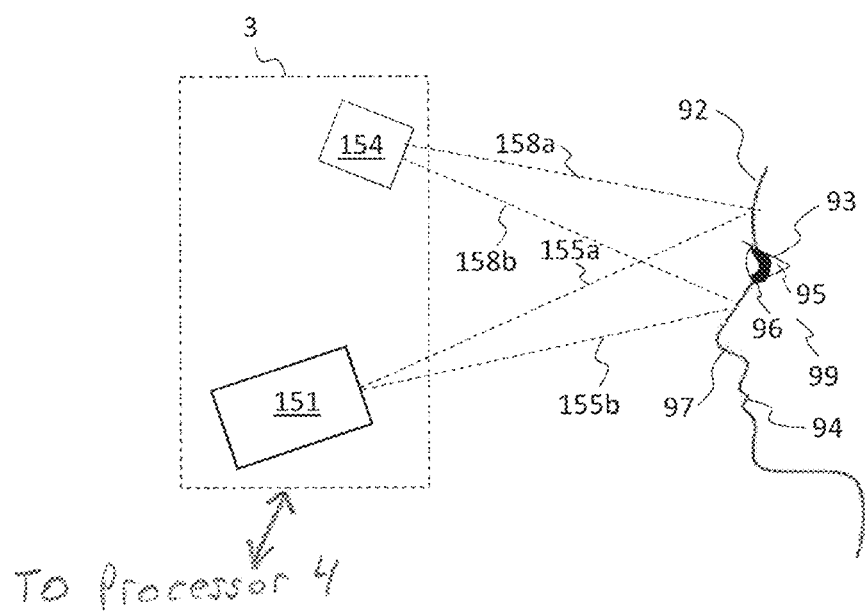
FIG. 10 is a block diagram of topology scanner of the system of FIG. 1 utilizing a structured light projector and imager.

Referring to FIG. 10, the topology scanner 3 of system 1 is illustrated utilizing a structured light imaging (SLI) scanner or module, which comprises a structured light projector 154 and an optional camera or imager 151. Wires or cables connect processor 4 to power and control projector 152 and receive images from imager 151 if present and other electronics of the SLI scanner of FIG. 10. With SLI metrology a series of patterned light illumination is projected within a certain FOV and a camera captures a series of images based upon the illumination of different patterns of light. The light patterning is generally a line or series of lines that may be binary or grayscale and may include patterns of different frequencies as well as different phases. By way of example, projector 154 may be one of DLP® LightCrafter products available from Texas Instruments Inc. (Plano, Tex.) which can display grayscale patterns at 120 Hz and binary patterns at >4000 Hz. These LightCrafter projectors operate with an array of DMD micro-mirrors to achieve 1 megapixel and greater resolution displays. The Texas Instruments Inc. projectors operate with a set of red, green, and blue LEDs to enable full-color visible displays. Texas Instruments Inc. has DMD micro-mirror arrays available with near infrared (NIR) tuned reflective coatings to provide structured light projector 154 that operates in the NIR portion of the spectrum. NIR, particular 800 nm and above is particular useful, so that structured light illuminating a subject's eye sometimes with a dark line and sometimes with a bright light does not cause unwanted eye reactions, such as rapid eye movement that might blur the eye image as well as not to cause the eye to blink and occlude the eye. SLI works by projector 154 projecting straight illumination lines on an object, where the resulting illumination lines overlaid on the object are observed by camera 151 at an angle relative to the structured light projector. If the structured light lines strike a flat surface, they will still appear straight in the image captured by camera 151, but depending upon the tilt of that flat surface, the observed curvature as well as the spatial frequency of the lines will be altered. If the structured light lines strike a curved object, they will appear curved in the camera 151 image. Based upon how the curvature and observed spatial frequency of a set of lines appear in a structured light image stack (where each image in the stack is taken by camera 151 when the projector 154 has a different structured light pattern on the object, e.g., different frequencies of straight lines, and/or different phases of a fixed illumination line frequency), structures or measurements for PA detection are made as described earlier at step 26. Thus, the structured light images outputted from camera 151 provide topology data received and stored in memory by processor 4 and/or optional computer 5 of the object being illuminated, i.e., one or more ocular or extraocular features, so that the topology of such object may be determined at step 26 for PAD detection. See incorporated U.S. Pat. No. 7,440,590 (Hassebrook et al.) for a discussion on SLI capture of the topology of an object. While imager 151 is shown in the topology scanner 3 of FIG. 10, the imaging of the projected structured light may also be captured by biometric scanner 2, making imager 151 not required. The camera needed for imager 151 may be similar to that described in reference to camera 124.

As described earlier, the directing of the topology scanner 3 to analyze certain locations of a biometric representation 92 at step 24 (FIG. 2A) may be a physical movement of the topology scanner 3, a movement of part of scanner 3, a beam steering, or a windowing of the region of interest. For the embodiment of a SLI operative topology scanner 3 depicted in FIG. 10, the entire scanner 3 might be moved through use of translation stages. For example, the SLI topology module might have a FOV denoted by dashed lines 155a and 155b for the imager 151 and 158a and 158b for the projector 154 that encompasses only a single eye, but biometric scanning 2 enables imaging of two eyes. Scanner 3 may then translate linearly in one axis to capture topology data for PAD analysis from one eye to the other eye. Alternatively, the SLI operative topology scanner 3 has a FOV which substantially overlaps the FOV of biometric scanner 2, and rather than physically directing components of the topology scanner 3, the sensor of imager 151, if present, or of biometric scanner 2 may be windowed so that image data is only collected and analyzed about the location or locations of interest for PAD analysis. Windowing a sensor output to a smaller region of interest is a way of speeding up the frame rate of a sensor and thereby potentially enabling the topology data collection for PAD analysis to occur more rapidly. Alternatively, rather than performing this windowing or region of interest operation at the sensor level, it may performed at the image data level by processor 4 and/or optional computer 5 where image frames are first windowed to localize at selected location(s) determined at step 25 (FIG. 2) and then analyzed for the presence of PAs at step 26.

The topology scanner 3 of system 1 further may utilize a stereo vision camera system or module of earlier incorporated U.S. Pat. Nos. 4,924,506, 6,028,672, or 6,301,370. For stereo imaging, topology scanner 3 has two or more cameras take pictures of a iris and/or face of presentation 12 of the subject of FIG. 1, and through triangulation and image processing the processor 4 and/or optional computer 5 determine the location of an object, such as one or more ocular or extraocular objects, of the subject in 3D space.

Pixel locations on the two-dimensional image (biometric data) from the biometric scanner 2 are correlated spatially in memory (such as a look up table) of the processor 4 with FOV of the topology scanner 3, so that FOV of the topology scanner 3 can be moved at or along locations in the FOV of the biometric scanner 2. It is preferred that calibration of such spatial correlation, if needed, occurs at the factory and not in the field. By way of example, a calibration target can be placed in space within the FOV of both scanner 2 and 3 in system 1 much in the same way that fingerprint scanners are certified currently for the FBI. These targets can contain lines of specific spatial frequencies as well as marks located at specific points in order to calibrate and adjust the imaging resolution of the two scanners 2 and 3 as well as their relative offsets in x, y and theta (rotation in the x-y plane between what the biometric scanner may deem the x axis to be and what the PAD module deems the x-axis to be). Such targets can be printed onto Mylar sheets, photographic paper or fabricated with lithographically patterned and etched chrome on glass, such as from Applied Image, Inc. (Rochester, N.Y.).

Optionally, the biometric scanner 2 can be removed from system 1, if the topology scanner 3 can also provide a biometric scanner, where biometric data for determining location(s) for PAD, 3D topology, and biometric detection are provided by the same module/unit in system 1 for use by the processor 4 and/or optional computer 5, as may be the case when topology scanner 3 is provided by a stereo vision camera system or module described earlier.

In summary, the present invention provides a system, apparatus, and method that comprises a biometric scanner 2 that identifies potential presence of an iris or face biometric presentation within the scanner's field of view (FOV), and having topology scanner 3 by which the 3D topology of objects within its FOV can measure at identified location(s) of a potential face or iris presentation and then centers its 3D topological investigation around this/these location(s). Preferably, the 3D topological investigation conducted by system 1 analyzes the shape of the cornea and iris in order to determine if the biometric presentation is likely to be a true or a false biometric representation. The system 1 has software, firmware, and hardware of processor 4 and/or optional computer 5 to make the comparison and generating a presentation attack (PA) score, where, by way of example, such score might range from 0 to 100 with a score of 0 representing a very high probability that the biometric presentation is true (i.e., from a human, preferably a living human) and a 100 implying a very high probability that the biometric presentation is false (i.e., a constructed artifact made to at least in some ways mimic a true biometric presentation).

Using the results, i.e., image data, of a 3D topological investigation by the apparatus processor(s) the shape of the sclera (step 201) is analyzed to determine if the biometric presentation is likely to be a true or a false biometric representation. For example, the shape of the sclera may be determined to be curved and not flat, such as by using a structured light projector and optically projecting at an angle to the eye straight lines of light and determining if they stay flat across the sclera or appear curved when observing said lines at an angle relative to the projector. The sclera shape analysis may use more precise 3D collected data of the sclera to include curve fitting of the measured sclera shape to a best fit sphere and compare this to the range of what is expected for human eyes, for example a best fit sphere radius. The sclera shape analysis may use very precise 3D mapping data of the sclera in order to determine the freeform profile of the biometric representations sclera and determine if it is within range of what is expected for humans as stored in memory of, or accessible to, processor 4, which if outside such range may indicate a PA. Consider FIGS. 4 and 5 from optical coherence tomography (OCT) data collected by Lee et al. cited earlier, the sclera is not a sphere, nor is it symmetrical. As depicted in FIG. 5, the human eye has a topology that is different on the nasal side compared to the temporal side and on each side has an aspheric profile since the local radius of curvature changes as a function of distance away from the center of the pupil.

Further, PAD performed by the processor 4 and/or optional computer 5 at step 26 may look at the topology of the iris (step 202). Seal et al. cited earlier discusses looking for a flat iris versus a curved iris in order to distinguish a real iris from that of a fake iris printed onto a contact lens which then conforms to the profile of the hacker's cornea. However, Seal et al. does not require that the actual profile of the iris be measured, only that it appears curved. In this manner, a flat iris that might be a painted or printed iris on the plano side of a plano-convex glass or plastic lens would pass the PAD teachings of Seal et al. This problem is solved by system 1 of the present invention by performing PAD which may also include analysis of very precise 3D topology data wherein the profile of the iris is measured. Though relatively flat, the iris has a series of folds and undulations when observed on a more microscopic scale, as described earlier in connection with FIG. 7. The measurement and observance of these fine details of the iris in topology data obtained from the topology scanner 3 can be used in arriving at a PA score (step 209).

The PAD performed by processor 4 and/or optional computer 5 may use the topology of the eye outside of just the sclera and the iris (steps 200, 203-205). By way of example, the topology and presence of the eyelids, eyelashes, the lacrimal caruncle and the nose can be used for PAD. By way of example, PAD looks for the step in profile between the sclera and where either the upper or lower eyelid or both begin to cover the sclera. The PAD compare that measured step profile to the expected thickness of eyelids for humans. Further, the PAD performed by processor 4 and/or optional computer 5 may use fusion to fuse (or combine) the metrics of sclera curvature, iris topology, as well as analysis of eyelids, eyelashes, eyebrows, lacrimal caruncle, or any other eye feature that is being analyzed in order to arrive at an overall PA score of the biometric presentation under question. Fusion of scores or metrics may be performed.

Variations and modifications in the system, apparatus, and method for biometric security, and in particular for presentation attack detection in an iris or face scanner as illustrated herein will undoubtedly become apparent to those skilled in the art. Accordingly, the above description should be taken as illustrative and not in a limiting sense.

The invention claimed is:

1. A system for biometric security comprising:
   a biometric scanner for capturing biometric data over a first field of view of a subject having at least one eye of the subject;
   a topology scanner; and
   one or more processors utilizing said biometric data received from said biometric scanner to select one or more locations within the first field of view indicative of a biometric presentation to the biometric scanner, directing said topology scanner to capture topology data over a second field of view of the subject at one or more of said selected one or more locations, and determining in accordance with said topology data captured when said first field of view contains a possible fake presentation to said biometric scanner.

2. The system according to claim 1 where the biometric scanner is one of an iris or face scanner.

3. The system according to claim 1 wherein said topology scanner utilizes an optical coherence tomography imager to scan said one or more of said selected one or more locations along the at least one eye of the subject or face of the subject to obtain said topology data.

4. The system according to claim 3 wherein said optical coherence tomography imager has optics comprising a movable mirror for directing a beam to scan and collect returned light from each of said one or more of said selected one or more locations.

5. The system according to claim 1 wherein said topology scanner utilizes a laser scanner to scan said one or more of said selected one or more locations along the at least one eye of the subject or face of the subject to obtain said topology data.

6. The system according to claim 5 wherein said laser scanner has optics comprising a movable mirror for directing a beam to scan and collect returned light from each of said one or more of said selected one or more locations.

7. The system according to claim 1 wherein said topology scanner utilizes one of a structured light imager, confocal scanner, or stereo scanner to scan said one or more of said selected one or more locations along the at least one eye of the subject or face of the subject to obtain said topology data.

8. The system according to claim 1 wherein said one or more processors utilizes said topology data to determine three-dimensional measurements of one or more of eye shape, sclera, iris, and caruncle to differentiate said subject between being fake and real.

9. The system according to claim 1 wherein said one or more processors utilizes said topology data to determine three-dimensional measurements of one or more of eyelid, nasal area, eyebrows, and eyelashes to differentiate said subject between being fake and real.

10. The system according to claim 1 wherein said one or more processors receives said topology data associated with at least one of said selected one or more locations to determine a best fit aspheric toroid of a sclera of the subject to differentiate said subject between being fake and real.

11. The system according to claim 1 wherein said one or more processors receives said topology data associated with at least one of said selected one or more locations to determine a best fit aspheric toroid of one or both a temporal side and a nasal side of a sclera of the subject to differentiate said subject between being fake and real.

12. The system according to claim 1 wherein said one or more processors receives said topology data associated with at least one of said selected one or more locations for aspheric free-form mapping of one or both of temporal and nasal parts of a sclera of the subject to differentiate said subject between being fake and real.

13. The system according to claim 1 wherein said one or more processors determines one or more measurements associated with an iris of the subject from using said topology data of at least one of said selected one or more locations to differentiate said subject between being fake and real.

14. The system according to claim 1 wherein said one or more processors receives said topology data associated with at least one of said selected one or more locations to enable measurement of thickness of an eyelid to differentiate said subject between being fake and real.

15. The system according to claim 1 wherein said second field of view overlaps at least a portion of said first field of view, and said first and second fields of view are spatially correlated with each other for enabling said one or more processors to direct said second field of view of said topology scanner to said selected one or more locations.

16. The system according to claim 1 wherein:
   the selected one or more locations comprise a sclera of an eye of the subject and said topology data captured comprises topology data representative of the sclera; and
   determining in accordance with said topology data captured when said first field of view contains a possible fake presentation to said biometric scanner comprises determining one or more measurements of the sclera in accordance with said topology data representative of the sclera and comparing said one or more measurements with one or more of a threshold or range expected of a human sclera.

17. A method for biometric security comprising the steps of:

capturing biometric data with a biometric scanner over a first field of view of a subject having at least one eye of the subject;

selecting one or more locations using said biometric data within the first field of view indicative of a biometric presentation to the biometric scanner;

directing a topology scanner to capture topology data over a second field of the subject at one or more of said selected one or more locations; and determining in accordance with said topology data captured when said first field of view contains a possible fake presentation to said biometric scanner.

18. The method according to claim 17 wherein said directing step further comprises capturing said topology data using said topology scanner operative by one of optical coherence tomography, laser scanning, structured light imaging, confocal scanning, or stereo scanning.

19. The method according to claim 17 wherein said capturing biometric data over said first field of view is carried out by a biometric iris or face scanner.

20. The method of claim 17 wherein:

the selected one or more locations comprise a sclera of an eye of the subject and said topology data captured comprises topology data representative of the sclera; and determining in accordance with said topology data captured when said first field of view contains a possible fake presentation to said biometric scanner comprises determining one or more measurements of the sclera in accordance with said topology data representative of the sclera and comparing said one or more measurements with one or more of a threshold or range expected of a human sclera.

* * * * *